United States Patent [19]

Hallberg

[11] Patent Number: 5,070,016

[45] Date of Patent: Dec. 3, 1991

[54] INTEGRATED PROCESS FOR PRODUCING ETHANOL, METHANOL AND BUTYL ETHERS

[75] Inventor: David E. Hallberg, Norcross, Ga.

[73] Assignee: Revolution Fuels of America, Inc., Atlanta, Ga.

[21] Appl. No.: 676,821

[22] Filed: Mar. 28, 1991

[51] Int. Cl.$^5$ .................... C12P 7/00; C12P 7/14; C12P 7/06; C12P 7/02

[52] U.S. Cl. .................................. 435/132; 435/155; 435/157; 435/161; 435/162; 435/813; 435/822

[58] Field of Search ............... 435/162, 161, 132, 155, 435/157, 822, 813

[56] References Cited

U.S. PATENT DOCUMENTS

| | | | |
|---|---|---|---|
| 4,118,425 | 10/1978 | Herbstman | 568/697 |
| 4,334,026 | 6/1982 | Chynoweth | 435/163 |
| 4,413,150 | 11/1983 | Briggs | 568/697 |
| 4,425,433 | 1/1984 | Neves | 435/161 |
| 4,476,334 | 10/1984 | Chen et al. | 568/902.2 |
| 4,617,270 | 10/1986 | Anderson et al. | 435/161 |
| 4,680,263 | 7/1987 | Yamada et al. | 435/162 |
| 4,731,329 | 3/1988 | Lawford | 435/162 |
| 4,816,607 | 3/1989 | Vora et al. | 568/697 |
| 4,885,241 | 12/1989 | Millichip | 435/162 |
| 4,894,394 | 1/1990 | Van Dijk et al. | 518/700 |

Primary Examiner—Herbert J. Lilling

[57] ABSTRACT

A methanol synthesis and an ethanol synthesis are integrated into a single continuous process with the by-product carbon dioxide generated in the ethanol synthesis being utilized in the methanol synthesis. The methanol synthesis and ethanol synthesis can be further integrated with isobutylene synthesis with by-product hydrogen formed during isobutylene synthesis being used as a raw material in the methanol synthesis. In the preferred embodiments the ethanol synthesis utilizes *Zymomonas mobilis* bacteria in anaerobic fermentation in order to maximize the amount of carbon dioxide produced in a form which can be utilized in the methanol synthesis, to reduce carbon dioxide emissions and to provide an ethanol product which is highly suitable for reaction with the isobutylene to form ethyl tertiary butyl ether.

16 Claims, 2 Drawing Sheets

INTEGRATED PROCESS FOR PRODUCING ETHANOL, METHANOL AND BUTYL ETHERS

BACKGROUND OF THE INVENTION

1. Field of the Invention

The present invention relates to a novel integrated process for production of oxygenated compounds (alcohols and ethers) for motor fuel use.

2. Background of the Prior Art

In order to reduce air pollution, public policy dictates reductions in pollutants arising from the operation of motor vehicles powered by petroleum derivatives, especially motor fuel gasoline. The first major act was the virtual elimination of tetraethyl lead as a motor gasoline octane improver, which has resulted in definite, and measurable, reductions in the amount of poisonous lead emitted into the atmosphere. At the same time, refiners were obliged to replace lost performance by increasing motor gasoline octane levels by other means. Refiners placed primary emphasis on increasing the severity of reforming and also added octane-enhancing chemicals, including more butanes; more aromatics (benzene, toluene and xylene); and alcohols (especially ethanol) and ethers (especially methyl tertiary butyl ether, or MTBE).

The outcome has been to successfully replace the lost anti-knock octane value from lead's disappearance, but concurrently, largely due to the increased reforming severity and higher levels of volatile butanes, the result has been to increase the evaporation of organic materials; to increase emissions of ozone-forming materials which cause urban smog; and to increase the aromatic content of motor gasoline, which leads to increased emissions of benzene, a known carcinogen. There is also the problem of increased emissions of poisonous carbon monoxide caused by the incomplete combustion of motor gasoline.

Legislation has been enacted in the U.S. (and other industrialized countries) which mandates certain fuel characteristics in order to control deleterious emissions. Such legislation characteristically stipulates reductions in fuel volatility; carbon monoxide emissions; ozone-forming chemicals; aromatic content; and toxic emissions. One of the primary means of achieving these reductions has been to specify minimum oxygen levels in all motor gasoline sold in certain locations and at certain times of the year (in some cases, year-round).

These mandated changes in the composition of motor gasoline will require significant increases in the amounts of oxygenated fuel materials being produced, especially:
methanol as a component of MTBE;
methanol for use in an 85:15 methanol: gasoline blend (primarily in California);
ethanol as a highly oxygenated material to be added to finished gasoline at the downstream end of the distribution chain; and
ethanol as a component of ethyl tertiary-butyl ether (ETBE).

Large increases in the production of isobutylene to react with ethanol and methanol in producing ETBE and MTBE will also be required.

Ethanol Production

Fuel ethanol is currently commercially produced by yeast fermentation of fermentable sugars produced from starches, principally from corn. The carbon dioxide is often recovered and processed by third parties to be used in freezing poultry, making dry ice, in fire extinguishers, in recovering petroleum from "played out" wells by pressurizing them, etc. The value of crude carbon dioxide is low, normally $5.00 to $8.00 per ton, and in some locations there is no market for it at all.

Furthermore, the inherent characteristics of the yeasts used in producing ethanol require that they go through an aerobic stage to multiply followed by an anaerobic stage to produce ethanol. The carbon dioxide from the first state thus contains considerable amounts of air, which is uneconomical to remove in most cases. See, for example, column 1, lines 18-64 of U.S. Pat. No. 4,731,329 and column 1, lines 10-22 of U.S. Pat. No. 4,885,241. In addition, the metabolism of the yeast produces materials other than ethanol in significant amounts, including "fusel oils", "aldehydes", and especially "glycerol", which markedly reduce the amount of ethanol obtained from a given amount of sugar.

Methanol Production

Methanol is typically produced in essentially self-contained production facilities, which typically use natural gas (usually predominantly methane) and water as the basic raw materials. The process includes two basic steps: formation of "syngas" from methane and water, and synthesis of the methanol by reacting the syngas in the methanol reactor. The basic reactions are:

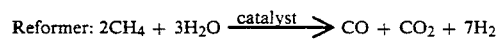

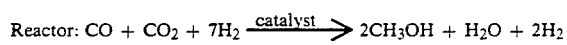

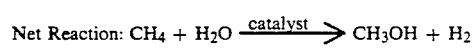

Natural gas is used not only as a reactant, but is also burned as a fuel to heat the reformer stage. In the reactor stage only a portion of the methanol synthesis takes place in one pass, so methanol is removed and unreacted materials are recycled. To prevent build-up of inert materials, a portion of the recycle gas is purged and its combustible content is also burned to heat the reformer.

In large U.S. plants, which are generally highly efficient, the natural gas-to-methanol yield on a carbon basis is about 67%, and the heat value of the methanol (HHV) is only about 71% of the natural gas consumed. Furthermore, the cost of the natural gas represents a significant portion of the total plant cost.

In the methanol synthesis shown above, it should be noted that the carbon, oxygen, and hydrogen are not in stoichiometric balance for methanol, there being an excess of hydrogen. When a supply of carbon dioxide is available, it is often added to the natural gas feed to correct the imbalance:

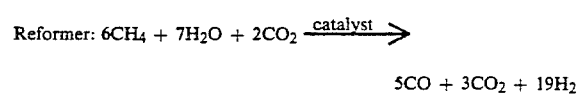

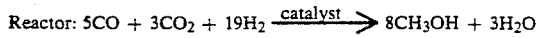

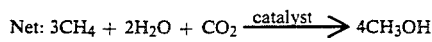

The addition of carbon dioxide to react with the excess hydrogen has thus reduced the amount of natural gas used per molecule of methanol from one to 0.75. However, this also reduces the hydrogen purge to heat the reformer, increasing its use of natural gas fuel somewhat. However, there is a net reduction in total cost.

Isobutylene Production

Isobutylene may be obtained in different ways. In petroleum refineries, off-gas from the fluid cat-cracker contains a mixture of butanes, normal, iso-, and isobutylene. If this mixture is passed over an acid catalyst with methanol, the methanol reacts with the isobutylene to form MTBE, while the remaining butanes are unreacted and are returned to the refinery. The reaction is a simple addition:

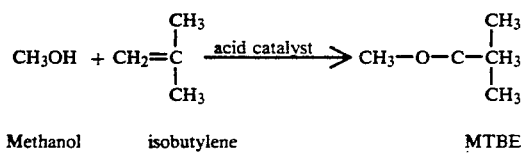

Methanol    isobutylene            MTBE

Isobutylene may also be obtained as a byproduct of propylene oxide manufacture. However, the increased demand for isobutylene as a feedstock for tertiary butyl ethers has used up most of the easily available quantities, and it is now necessary to produce it from isobutane by dehydrogenation:

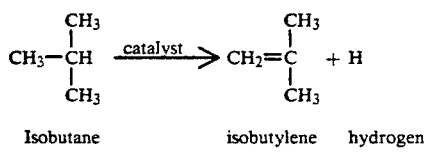

Isobutane      isobutylene    hydrogen

In practice, the hydrogen stream from this reaction contains, depending upon the specific process, additional quantities of hydrocarbons, ranging from $C_1$ to $C_4$ including normal, iso, alkane, or alkene forms. The stream is usually used as fuel in the refinery or chemical plant.

The iso-butane discussed above normally is recovered from natural gas liquids, which contain both normal and isobutane forms, by firms that specialize in these separations. However, if isobutane is not available, mixed iso- and normal butanes may be purchased and converted to all iso- in a special unit preceding dehydrogenation. This step requires very large amounts of steam energy.

ETBE

ETBE (ethyl tertiary butyl ether) is produced by reacting ethanol, instead of methanol, with isobutylene over an acid catalyst. At present there are no dedicated units, but the product has been made in MTBE plants and in special pilot plants.

MTBE

MTBE, methyl tertiary butyl ether, being produced today is generally produced in refineries which combine their own isobutylene production with purchased methanol, or by companies with other sources of isbutylene who react it with purchased methanol. In any event, the raw materials have historically come from discrete, non-integrated sources. However, integration of methanol and isobutylene manufacture has recently been suggested by "Now, MTBE from Butane", by Muddarris et al, Hydrocarbon Processing. October 1980.

Although MTBE has preempted the market for refinery-added oxygenates, there is a real need for others such as ETBE (or TAME, ETAE) to supplant or to be blended with MTBE. The following table highlights some of the more critical physical characteristics of MTBE and ETBE:

|  | MTBE | ETBE |
|---|---|---|
| Oxygen - wt. % | 18.2 | 15.7 |
| Boiling Point - F. | 133 | 163 |
| Blending RVP - psi | 8.0–9.0 | 3.5–4.5 |
| Blending Octane - (R + M)/2 | 107 | 112 |

Although ETBE has a lower oxygen content than MTBE, it has a desirably higher octane value and lower vapor pressure. ETBE also has the advantage of being less reactive with automotive plastics and pipeline gasket material (e.g., less swelling of elastomers, etc.). Blends of the two ethers give better distillation curves than either separately.

SUMMARY OF THE INVENTION

It is an object of the present invention to integrate the production of ethanol and methanol, and, optionally, tertiary butyl ethers, in a novel way that reduces the manufacturing costs of methanol and products derived therefrom by using by-product carbon dioxide from the production of ethanol.

Another objective of the present invention is to replace a non-renewable raw material, i.e. natural gas methane, with a renewable carbon oxide source, i.e. by-product carbon dioxide resulting from the manufacture of ethanol from renewable fermentable vegetable materials.

Another objective of the present invention is to replace yeast fermentation conventionally used in the production of ethanol with fermentation by bacteria such as *Zymomonas mobilis* in order to produce a by-product carbon dioxide uniquely suited to the production of methanol.

A further object of the present invention is to reduce the level of carbon dioxide emissions often associated with the production of ethanol and thereby provide a process for ethanol production more compatible with public policy concerns regarding the so-called "greenhouse effect."

Yet another object of the present invention is to provide an integrated process for the production of methyl and ethyl tertiary butyl ethers suitable for use as fuel additives.

At its broadest aspect, the present invention involves the integration of ethanol production with methanol production in such a way as to achieve economies in both processes heretofore unattainable. More specifically, the present invention utilizes by-product carbon dioxide formed in the production of ethanol as a raw material for producing methanol. Further, the excess process heat from the methanol synthesis is utilized to generate steam which provides at least a portion of the energy required for ethanol production by fermentation. The present invention also involves the discovery that bacterial fermentation for the production of ethanol is uniquely suited to integration with methanol production and with the production of an ethanol product suitable for use in reaction with isobutylene for the production of ethyl tertiary butyl ether (ETBE).

Accordingly, the present invention provides an integrated process for the simultaneous, separate production of ethanol and methanol. The process includes fermenting a vegetable material anaerobically in an aqueous medium to produce ethanol in the medium and by-product carbon dioxide containing less than 1% by volume air. The ethanol is recovered from the aqueous medium and, optionally, further reacted with isobutylene to form ETBE. The by-product carbon dioxide containing less than 1% by volume air is reacted with hydrogen resulting in the formation of methanol. The exothermic heat of reaction of the methanol synthesis, as well as heat from other process streams, is recovered by heat exchange between the intermediate products from the methanol synthesis and water, resulting in a generation of steam which is then utilized in the production of ethanol.

In the preferred embodiments, the ethanol fermentation is effected utilizing the bacterium *Zymomonas mobilis*. This preferred fermentation has been found to be uniquely suited to applicants' integrated process both from the point of view of producing a by-product carbon dioxide suitable for use in the production of methanol, with minimum purge of carbon dioxide fractions containing excessive amounts of air, and from the point of view of producing an ethanol product containing less by-products having a deleterious effect in the production of MTBE by reaction with isobutylene.

In one preferred embodiment the present invention is integrated with a process for the production of isobutylene from n-butane. In this preferred embodiment a further savings is achieved by utilization of the by-product hydrogen produced in isobutylene manufacture for reaction with the by-product carbon dioxide in the methanol synthesis. Prior to utilizing this hydrogen stream in the production of methanol, quantities of higher molecular weight organics, particularly olefinic compounds, must be removed. The cleaning of the hydrogen can be accomplished by one of two methods: (1) the deleterious compounds can be removed for sale or utilized in supplementing fuel gas or (2) the olefinic compounds can be converted to aliphatics, eliminating the related problems and thereby further reducing the demand for methane feed to the methanol synthesis reactor.

DESCRIPTION OF THE PREFERRED EMBODIMENTS

Figure 1:
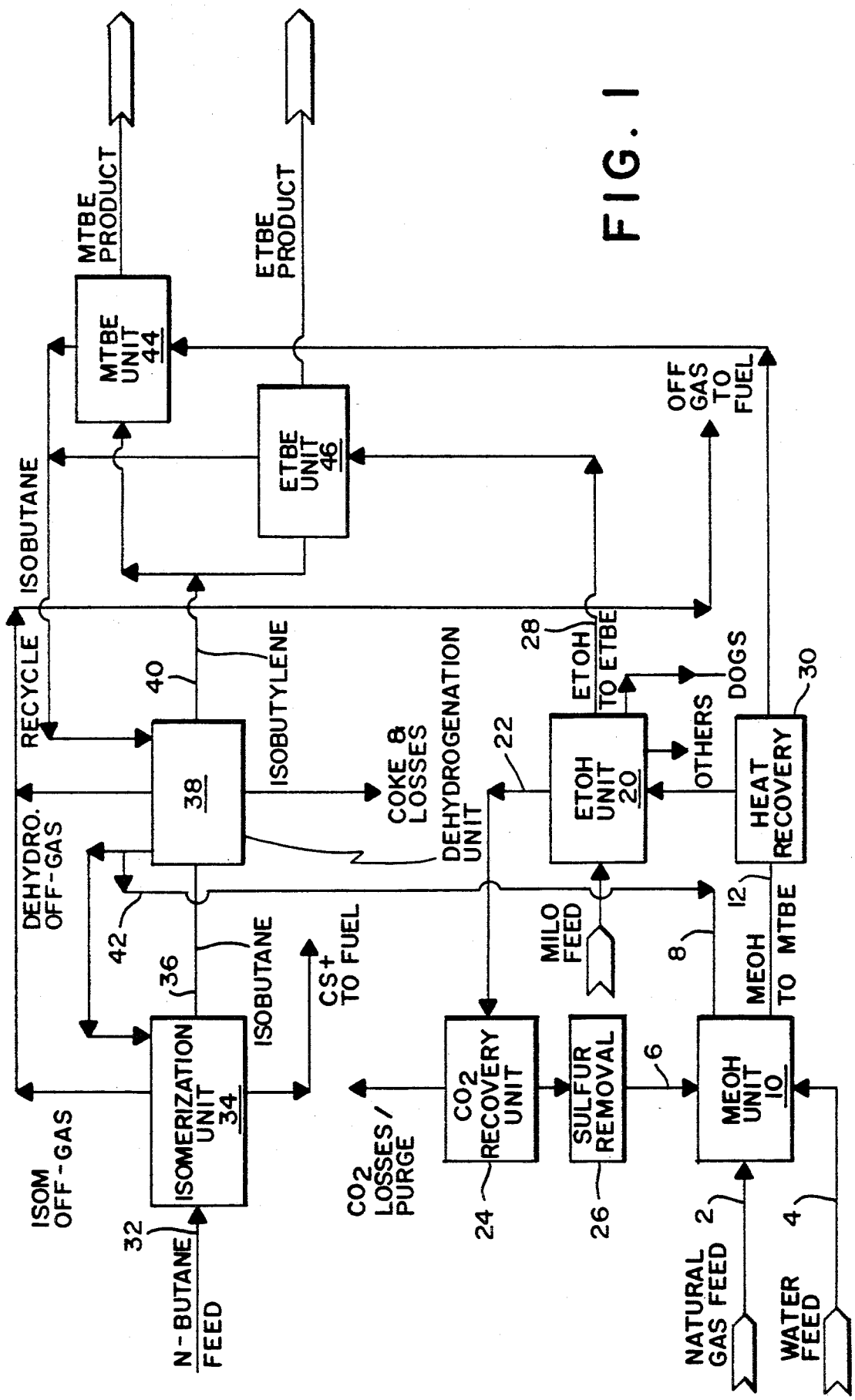
FIG. 1 is a flow chart of a preferred embodiment of the present invention in which syntheses for the production of methanol, ethanol and isobutylene are integrated for the production of MTBE and ETBE.
Figure 2:
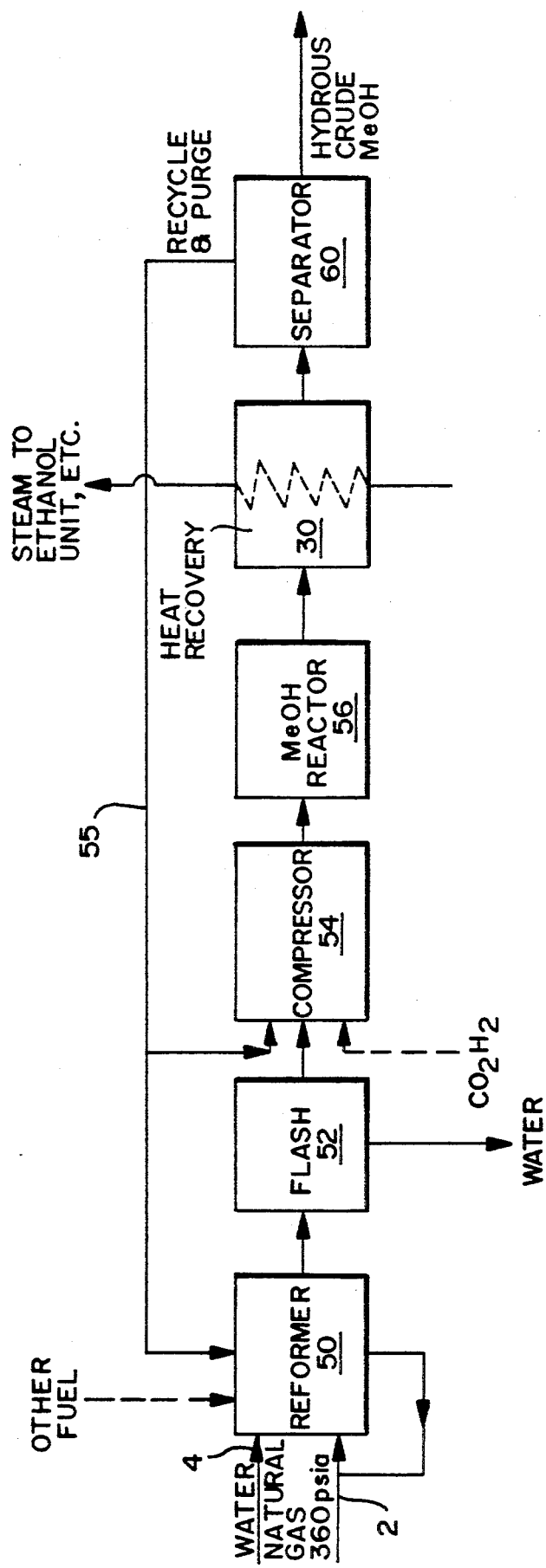
FIG. 2 is a flow chart of a preferred embodiment of the present invention for methanol synthesis.

In FIG. 1 10 represents the methanol synthesis plant which is illustrated in detail in FIG. 2 and, as shown in FIG. 2, consists of a number of different units. Natural gas is introduced at 2 and water at 4 for steam reforming to form a synthesis gas (hereinafter "syngas") which, along with by-product carbon dioxide introduced at 6 and by-product hydrogen introduced at 8, is converted to methanol which exits at 12. The ethanol unit 20 is preferably multiple fermenters containing the bacteria *Zymomonas mobilis*. The by-product carbon dioxide produced by fermentation exits at 22 and is compressed from about two inches $H_2O$ gauge to about 350 psig in a carbon dioxide recovery unit 24. From recovery unit 24 the carbon dioxide is routed to the methanol unit 10 through a sulfur removal treatment 26 (sulfur containing gases are removed from the by-product carbon dioxide in a conventional manner, e.g. by pressure swing adsorption (psa) or by membrane separation). An ethanol product exits at 28. Heat from the reforming and/or methanol synthesis reactions is recovered, e.g. in heat recovery unit 30, and utilized, for example, in the ethanol production units schematically illustrated at 20. Thus, the ethanol production process and the methanol production process are integrated with the ethanol production process supplying by-product carbon dioxide for methanol synthesis and the methanol synthesis providing heat, typically in the form of steam, for the milling and mashing, distillation, evaporation and/or distillers dried grains with solubles (DDGS) drying steps involved in ethanol production and DDGS recovery by fermentation.

FIG. 1 also illustrates the further integration of ethanol synthesis units 20 and the methanol synthesis units 10 into a process for the production of tertiary butyl ethers. N-butanes are introduced at 32 into an isomerization unit 34 wherein the n-butane is converted into isobutane exiting at 36. The isobutane is fed to a dehydrogenation unit 38 which produces isobutylene which exits at 40 and a by-product hydrogen gas which exits at 42. The by-product hydrogen gas is fed, after clean up, via 42, to the isomerization unit 34, and via 8 to the methanol production units 10, thus integrating the isobutylene synthesis with the methanol synthesis. In the event isomerization is not integrated into the complex, more by-product hydrogen is available for purification and use in the methanol production unit 10. The isobutylene product 40 is then reacted with methanol in the MTBE unit 44 and/or with ethanol in the ETBE unit 46. Both MTBE and ETBE find utility as gasoline additives.

FIG. 2 illustrates the methanol synthesis 10 in greater detail. As seen in FIG. 2 water 4 and natural gas 2 are introduced into a steam reformer 50. The result is a syngas product which is introduced into flash tank 52 to separate water and then into the suction side of a compressor 54, along with recycled gas 55 from the crude methanol separator 60 and by-product carbon dioxide from ethanol synthesis and purified hydrogen gas from the dehydrogenation unit 38. The compressor 54 compresses the admixture to approximately 1500 psia and feeds it into the methanol reactor wherein a catalytic conversion to methanol is effected. The methanol product is then routed through a heat recovery unit 58 which generates steam for use in the ethanol synthesis or elsewhere in the integrated process. The methanol product stream is subsequently fed to a separator 60 which serves to separate hydrous crude methanol from the unreacted raw materials.

Several of the key unit processes shown in FIGS. 1 and 2 will now be discussed in greater detail below.

Methanol Synthesis

Compressed natural gas feed (primarily methane) is desulfurized, saturated with steam and catalytically reformed over a nickel reforming catalyst to convert the methane to synthesis gas (primarily carbon monoxide, carbon dioxide and hydrogen) utilizing conventional technology. The reforming reaction occurs at about 250-300 psig and 1600° F. in the steam reforming furnace. The reformer-furnace stack gases pass through thermal recovery facilities where high pressure steam is generated which in turn is utilized to drive large syngas compressors.

The methanol synthesis of the present invention departs from the prior art in that it utilizes by-product carbon dioxide, containing less than 1% air, derived from ethanol synthesis by fermentation. The by-product carbon dioxide may be fed to the reformer, along with the steam and natural gas. Preferably, the by-product carbon dioxide is fed to the suction side of the methanol synthesis gas compressor. The syngas exiting the reformer must be cooled from about 1600° F. to about 100° F. (at 250-300 psig) prior to compression to 1,100 psig. Blending of the synthesis gas with the by-product carbon dioxide, and optionally by-product hydrogen, offers a number of advantages as compared to the feeding of these by-product gases to the reformer. Firstly, the blending downstream of the reformer allows use of a smaller reformer with consequent savings in capital costs. Secondly, the blending may be used to furnish a part of the requisite cooling of the synthesis gas. Thirdly, blending downstream of the reformer increases the concentration of the carbon dioxide in the synthesis gas stream with a related increase in reaction rate which serves to reduce the recycle rate for the methanol reactor. Fourthly, this preferred approach allows use of higher reliability centrifugal compressors in contrast to use of reciprocal compressors. Fifthly, if the flow of by-product gas is interrupted, the stable operation of the reformer is unaffected.

The by-product carbon dioxide should be air free, preferably 1% air or less, in order to minimize: (1) the likelihood of side reactions, (2) poisoning of the catalyst, and (3) purge gas volumes.

The capacity of the methanol synthesis reactor in terms of utilization of by-product carbon dioxide can be increased, if desired, by co-blending with hydrogen. In a preferred embodiment of the present invention by-product hydrogen, produced by conversion of isobutane to isobutylene, is desulfurized and then blended with the by-product carbon dioxide and synthesis gas at the suction side of the methanol reactor compressor. Desulfurization is effected in a conventional manner, e.g. by pressure swing adsorption (PSA) or by membrane separation. Thus, in this preferred approach, methanol, ethanol and isobutylene synthesis are integrated in such a way to produce substantial raw material savings (primarily methane) and substantial reductions of emissions of carbon dioxide.

The synthesis gas, carbon dioxide and/or hydrogen, mixture is compressed to about 1,035 psig and enters the methanol synthesis gas recycle compressor where the pressure is increased to about 1,100 psig. Depending upon the exact design of the methanol unit, these pressures could vary slightly. This gas is now preheated and fed to the methanol synthesis reactor where the synthesis gas and by-product carbon dioxide are converted to methanol over a copper based catalyst utilizing conventional technology developed by ICI. See "The Methanol Synthesis: How Does it Work?", by Chinchen et al, *Chentech* (November 1990), the teachings of which are incorporated herein by reference. This conventional technology utilizes a copper/zinc oxide/alumina or a copper/zinc oxide/chromia catalyst. Most preferably, the exothermic methanol synthesis reaction occurs at about 1,100 psig and 250° C. over a copper/zinc oxide/alumina catalyst. Methanol synthesis reactor effluent is cooled in thermal recovery facilities and sent to distillation facilities to produce the desired methanol product, e.g. for use in MTBE synthesis. Unconverted synthesis gas is recycled to the methanol synthesis reactor.

The reactions of by-product $CO_2$ forming the methanol are:

$$CH_4 + CO_2 + 2H_2 \rightarrow 2CH_3OH + \Delta \tag{I}$$

$$3H_2 + CO_2 \rightarrow CH_3OH + H_2O + \Delta \tag{II}$$

In the integrated process of the present invention the combined "hydrogen stream" from isomerization and dehydrogenation, when combined with by-product $CO_2$, replace up to 100% (in terms of heating value) the amount of natural gas required for methanol production.

In conventional processes methane is the primary raw material and, as a consequence, constitutes the primary source of the carbon oxides for methanol formation. In contradistinction, in the process of the present invention by-product $CO_2$, e.g. from an ethanol fermentation unit, will constitute at least 50%, and preferably more than 60% of the carbon oxides to be reacted with the hydrogen from the dehydrogenation unit over a catalyst. As a consequence, the feed to the methanol catalytic converter will contain a higher ratio of $CO_2$ to CO as compared with synthesis gas. The higher ratio of $CO_2$ to CO will increase the reaction rate of methanol synthesis. Potential benefits include lower recycle rates with a related savings in energy, and possible downsizing of the methanol converter.

Ethanol Synthesis

The ethanol synthesis unit 20 employs a fermentation process which preferably contains the bacterium *Zymomonas mobilis* and serves to produce ethanol by continuous cascade fermentation. A suitable continuous process for the production of ethanol by *Zymomonas mobilis* fermentation is described in U.S. Pat. No. 4,731,329 issued to Lawford, the teachings of which are incorporated herein by reference. All phases of fermentation with *Zymomonas mobilis* are conducted anaerobically and, accordingly, the carbon dioxide produced by fermentation will contain less than 1% by volume air. It is possible, at least in theory, to derive a by-product carbon dioxide stream containing less than 1% by volume air from the second stage of a two-stage yeast fermentation process as described at column 1 of U.S. Pat. No. 4,731,329 and column 1 of U.S. Par. No. 4,885,241. In such conventional two-stage yeast fermentation processes, the first stage involves propagation of the yeast under aerobic conditions and is referred to as the growth stage. In the second stage fermentation is conducted under anaerobic conditions to produce ethanol. However, in practice, a small amount of air or oxygen is typically added to the second stage in order to encourage yeast growth. Even if it were practical to conduct the second stage of a yeast fermentation under total anaerobic conditions, the result would still be a considerable loss of carbon dioxide from the first stage. In a conventional batch yeast fermentation, only 60-75% of the $CO_2$ is recoverable (depending on the plant) since the initial volumes of carbon dioxide are contaminated with air and must be purged. Of course, the purging of such volumes of carbon dioxide is undesirable both from the viewpoint of environmental pollution and from the viewpoint of conservation of resources, which conservation translates to lower production costs in the present invention where the by-product carbon dioxide is used as a raw material in the synthesis of methanol. In continuous yeast fermentation processes the initial (first stage) vessels require air to promote yeast growth and vent gases are not recoverable from these fermenters. Again, only approximately 60-75% of the carbon dioxide is recoverable.

Another advantage which accrues from use of Zymomonas fermentation in the integrated process of the present invention is that the ethanol produced by *Zymomonas mobilis* is superior to yeast derived ethanol because of its lower content of undesirable by-products and impurities such as fusel oils, aldehydes, etc., which are transformed during the etherification processes for the production of ETBE into undesirable by-products such as diethyl ethers.

Isobutylene from n-butanes

A mixed butane feedstock is first fed to a deisobutanisation (fractionation) column wherein the supply is separated into isobutane and n-butane and the n-butane split is then isomerized over a platinum on alumina catalyst as described, for example, in "Now, MTBE from Butane" by Muddarris et al, *Hydrocarbon Processing*, October 1980, pages 91-91, in UK Patent Application 2,080,297 by Rashid and Muddarris and in U.S. Pat. No. 4,816,607 issued to Vora et al, the teachings of all three of which references are incorporated herein by reference.

The combined isobutane streams are then fed to the dehydrogenation unit for conversion to isobutylene. The preferred butane dehydrogenation catalyst is a chromium oxide/alumina catalyst operated at 540° C. to 640° C. as described by Rashid and Muddarris in UK 2,080,297A. However, a platinum/tin/alkali metal dehydrogenation catalyst, as described by Vora et al in U.S. Pat. No. 4,816,607 is a viable alternative, as is almost any conventional dehydrogenation catalyst. The conventional HOUDRY ™ processes, specifically, the CATOFIN ™ and CATADIENE ™ process may also be employed to convert isobutane to isobutylene. HOUDRY ™, CATOFIN ™ and CATADIENE ™ are trademarks of United Catalysts, Inc.

Etherification

The alcohol feed (methanol and/or ethanol) is reacted with the isobutylene over an acid bed catalyst in a low temperature/low pressure process that yields a high octane, clean burning oxygenate. The use of an acid catalyst for the production of MTBE in general, and the use of sulfonated solid resin catalysts in particular, is described by Vora et al in U.S. Pat. No. 4,816,607.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. An integrated continuous process for the production of ethanol and methanol comprising:
   (a) fermenting a vegetable material anaerobically in an aqueous medium to produce ethanol in said medium and by-product carbon dioxide containing less than 1% by volume air;
   (b) recovering said ethanol from said aqueous medium;
   (c) reacting said by-product carbon dioxide containing less than 1% by volume air with hydrogen in a methanol reactor to form a gas stream containing methanol.

2. The integrated process of claim 1 wherein said fermenting is by bacteria.

3. The integrated process of claim 2 wherein said bacteria are *Zymomonas mobilis*.

4. The integrated process of claim 3 wherein said fermenting is conducted in at least one fermenter on a continuous basis, with continuous addition of a carbon source and continuous removal of medium, and wherein the removed medium is filtered to separate out said bacteria leaving an ethanol product stream, and said separated bacteria are returned to said fermenter.

5. The integrated process of claim 1 wherein the ethanol is recovered from the aqueous medium by distillation and at least a portion of the heat used for said distillation is the generated steam.

6. The integrated process of claim 1 further comprising:
   (d) reacting methane and steam in a steam reformer to form carbon oxides and at least a portion of said hydrogen and wherein said carbon oxides and said hydrogen portion are reacted in admixture with said by-product carbon dioxide in step (c) to form said gas stream containing methanol.

7. The integrated process of claim 3 further comprising:
   (d) reacting methane and steam in a steam reformer to form carbon oxides and at least a portion of said hydrogen and wherein said carbon oxides and said hydrogen portion are reacted in admixtures with said by-product carbon dioxzide in step (c) to form said gas stream containing methanol.

8. The integrated process of claim 6 wherein said by-product carbon dioxide is fed to said steam reformer for admixture with carbon oxides and hydrogen produced therein.

9. The integrated process of claim 6 wherein said by-product carbon dioxide is admixed with said carbon oxides and portion of said hydrogen exiting said steam reformer and wherein the admixture is fed to the methanol reactor.

10. The integrated process of claim 7 wherein said by-product carbon dioxide is admixed with said carbon oxides and portion of said hydrogen exiting said steam reformer and wherein the admixture is fed to the methanol reactor.

11. The integrated process of claim 9 further comprising:
   dehydrogenating isobutane to make by-product hydrogen and isobutylene; and
   admixing said by-product hydrogen with said admixture for reaction with said carbon oxides and by-product carbon dioxide in said methanol reactor.

12. The integrated process of claim 10 further comprising:
   dehydrogenating isobutane to make by-product hydrogen and isobutylene; and admixing said by-product hydrogen with said admixture for reaction with said carbon oxides and by-product carbon dioxide in said methanol reactor.

13. The integrated process of claim 11 further comprising:

reacting said ethanol and/or methanol with said isobutylene to produce a tertiary butyl ether.

14. The integrated process of claim 12 further comprising:

reacting said ethanol and/or methanol with said isobutylene to produce a tertiary butyl ether.

15. The integrated process of claim 1 further comprising:

dehydrogenating isobutane to make at least a portion of said hydrogen and isobutylene.

16. The integrated process of claim 1, further comprising:

contacting said gas stream with water in a heat exchange relationship to generate steam.

* * * * *